United States Patent [19]

Elves

[11] Patent Number: 4,718,897
[45] Date of Patent: Jan. 12, 1988

[54] NONWOVEN SURGICAL SPONGE WITH X-RAY DETECTABLE ELEMENT

[75] Inventor: John Elves, Venray, Netherlands
[73] Assignee: Chicopee, New Brunswick, N.J.
[21] Appl. No.: 777,142
[22] Filed: Sep. 18, 1985
[51] Int. Cl.⁴ .............................................. A61F 13/16
[52] U.S. Cl. ................................................... 604/362
[58] Field of Search ................ 604/362, 370; 128/156

[56] References Cited

U.S. PATENT DOCUMENTS

| | | | |
|---|---|---|---|
| 3,068,547 | 12/1962 | L'Hommedieu | 428/239 |
| 3,491,802 | 1/1970 | Mortensen et al. | 604/370 |
| 3,756,241 | 9/1973 | Patience | 604/362 |
| 3,867,935 | 2/1975 | Eisdorfer et al. | 604/366 |
| 3,911,922 | 10/1975 | Kliger | 604/362 |
| 4,068,666 | 11/1978 | Shiff | 604/362 |
| 4,185,626 | 1/1980 | Jones et al. | 128/156 |
| 4,645,499 | 2/1987 | Rupinskas | 604/362 |

FOREIGN PATENT DOCUMENTS 0839451  6/1960  United Kingdom ................ 604/362

Primary Examiner—John D. Yasko

[57] ABSTRACT

A surgical sponge constructed of a nonwoven fabric is provided with an integral x-ray detectable element in the form of an entangled roving which is positioned on one surface of the non-woven fabric. The fabric is produced by placing the x-ray detectable element atop a fibrous web and subjecting the roving and web to hydraulic entanglement to produce a patterned, nonwoven fabric.

18 Claims, 3 Drawing Figures

NONWOVEN SURGICAL SPONGE WITH X-RAY DETECTABLE ELEMENT

FIELD OF THE INVENTION

This invention relates to surgical sponges constructed of nonwoven fabric materials, and more particularly, to surgical sponges which include an x-ray detectable element as an integral part of the nonwoven fabric structure.

BACKGROUND OF THE INVENTION

It is common practice in the medical field to include a radiopaque element in surgical sponges so that such sponges can be detected by x-ray if inadvertently left in the body cavity following a surgical procedure. In this context, surgical sponges include folded gauze and nonwoven fabric swabs, woven and knitted laparotomy pads, and cotton balls.

A common x-ray detectable material used in conjunction with surgical sponges is a polymeric filament or ribbon loaded with an x-ray opaque filler material such as barium sulfate. Suitable polymeric materials include polyisobutylene, polyvinyl chloride and copolymers of vinyl acetate and vinyl chloride.

The x-ray detectable elements have been attached to the base sponge material by a variety of techniques. In the case of gauze swabs, a filament has been interwoven into the fabric of the gauze, or attached to the surface of the fabric and folded into the sponge construction. In the case of laparotomy sponges, an x-ray detectable ribbon has been enclosed in a seam stitched along one edge of the pad, and an x-ray detectable filament has been incorporated into the woven handle strap of the pad.

Securing an x-ray detectable element to a nonwoven sponge has presented a problem since nonwovens are produced continuously and at high speed and sewing or stitching the x-ray detectable filament to the nonwoven is not practical from a manufacturing point of view. Some success was had in attaching the x-ray detectable filament to the surface of the nonwoven, usually by heat fusing or resin bonding. Although the X-ray detectable element could be secured by these methods, the security of attachment was not sufficient to prevent the x-ray detectable element from being pulled off the fabric under some conditions of use.

Commonly assigned application U.S. Ser. No. 605,369 discloses a nonwoven surgical sponge with an x-ray detectable element as an integral part of the fabric construction. The x-ray detectable element, a yarn or monofilament, is entangled into the interior of a layer of entangled fibers, and, in the case of the monofilament, hot calendered to secure it within the fabric. In the process disclosed therein the x-ray detectable element is placed between two fibrous webs prior to entangling. The webs may comprise a percentage of fusible fibers.

It is an object of the present invention to provide a x-ray detectable nonwoven surgical sponge with a simple construction and method of manufacture. These and other objects of the present invention will be apparent from the ensuing description and claims.

SUMMARY

A surgical sponge comprising a nonwoven fabric having an x-ray detectable element as an integral part of the fabric construction is obtained by positioning one or more continuous lengths of an x-ray detectable roving atop a fibrous web, and subjecting the roving and web to hydraulic entanglement while supported on an apertured belt or a roll. The resulting fabric is a nonwoven having the x-ray detectable element positioned on one surface of the fabric, with the fibers of the roving entangled, and the fibers of the fabric intertwined with the fibers of the roving.

DESCRIPTION

The method of manufacture of the surgical sponges of the present invention include conventional hydraulic entanglement methods, consisting of providing a web of staple length fibers, positioning the web on a patterned, apertured belt or a roll, and subjecting the web while supported on the belt or roll to a plurality of high pressure hydraulic jets to entangle the fibers into a pattern conforming to that of the supporting belt. The roll may be apertured with a smooth or patterned surface, or nonapertured. The entangled fibers are thereupon separated from the belt and dried to produce a patterned nonwoven fabric. This method of manufacturing is described in detail in U.S. Pat. Nos. 3,068,547; 3,129,466; 3,485,706; 3,494,821; and 3,681,184 and is well known to those skilled in the art.

The nonwoven fabric may comprise any suitable combination of natural and/or synthetic textile materials including cotton, rayon, acrylics, polyester and nylon. A preferred fiber composition includes absorbent cellulosic fibers and fusible fibers, and a preferred method includes heating the fabric to thermobond the fusible fibers. Fusible fibers suitable for use in the present invention include polyster and polyamide fibers as well as other commercially available fusible fibers.

Figure 1:
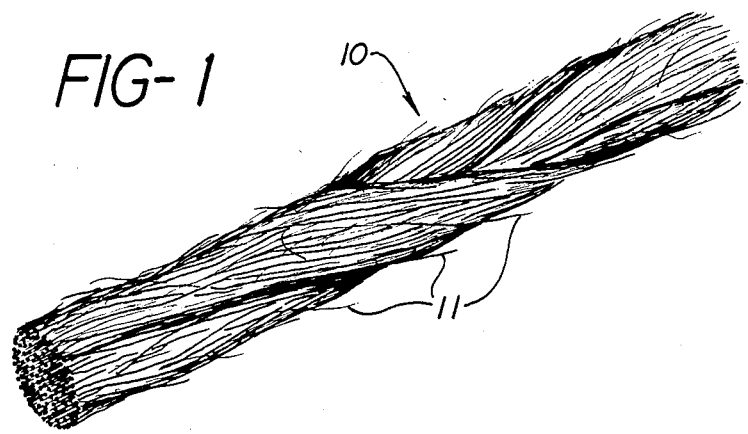
FIG. 1 is a view in perspective of a roving used to form the x-ray detectable element of the surgical sponge of the present invention.

The surgical sponge of the present invention utilizes an x-ray detectable roving rather than a yarn or monofilament. As shown in FIG. 1, the roving, 10, being substantially untwisted, has many free fiber ends, 11, for entangling with the fibers of the fibrous web. In addition the loose fibrous structure of the roving provides great ease of entangling of the fibers of the web into the roving. Because of the entangling enhancements, the roving need not be sandwiched between fibrous webs, but may be placed atop a fibrous layer and entangled therein. Indeed, because of the loose fibrous structure of the roving and its resulting weakness, in the method of the present invention, it is preferred to place the roving atop a fibrous web just prior to entangling, as to introduce the roving earlier in the process, such as before the addition of another web atop the roving, subjects the roving to unacceptable tension from the constantly increasing speeds of a continuous manufacturing line.

In the manufacture of the nonwoven fabrics of the present invention, a fibrous web is laid upon a moving apertured belt, and, one or more strands of a radiopaque, x-ray detectable roving are positioned atop the web. The web may comprise one or more layers of fibers. Fusible fibers may be present in one or more of the fiber layers, and in a preferred embodiment the web comprises 2%, or more preferably 4%, fusible fibers, which may be concentrated on the "belt-side" surface of the web or the layer of the web that is positioned against the apertured belt (or roll). In a particularly preferred method the fibrous web comprises a first layer, containing at least about 50% fusible fibers, and a second fibrous layer. In this preferred embodiment, the first layer may comprise 20% by weight of the combined weight of the first and second fibrous layers. In a most preferred construction, the first layer comprises a blend of fusible fibers and rayon fibers, and the second fibrous layer comprises rayon fibers. The first fibrous layer may be a random-laid or carded web; however, carded webs may be preferred at low basis weights to provide uniform web density. The second fibrous layer is preferably a random-laid web, to provide greater tear resistance in the final fabric. When, as preferred, the first layer is a carded layer of fibers, it is preferred that the first layer be positioned against the supporting apertured belt (or roll), the second fibrous layer positioned atop the first "belt side" layer, and the roving placed atop the second fibrous layer and spaced from the first ("belt side") layer. Use of this aforementioned laminate is preferred due to the difficulty of entangling the roving through a carded layer of fibers. The laminate is carried by the belt through the hydraulic entanglement process whereupon the fibers of the web are entangled to form a single thickness of nonwoven fabric with the x-ray detectable element entangled therein. The entangled nonwoven fabric may thereafter be subjected to the application of heat to heat fuse the thermoplastic fibers in the fabric. Heat may be applied by calendar rolls, through air bonding, or by passing the fabric about heated rolls.

The unified, nonwoven fabric preferably has a total dry weight of from about 0.7 to 3.0 ozs per square yard (20 to 100 g/m$^2$), with the lighter weights limited by the processability of the fibrous webs and the heavier weights limited by the desired utility and construction of the sponge, although higher weights may be preferred for some product applications such as laparotomy pads.

The x-ray detectable element is preferably dyed or pigmented blue or other suitable color which contrasts sharply with blood. The color permits ready identification of the x-ray detectable element in the sponge, facilitates sponge counting in the operating room and further helps locate the sponge when saturated with blood during use. As the x-ray detectable element is entangled on the hydraulic jet side of the fabric as compared to the belt side, it is consequently visually more apparent from that side. This increased visibility may be capitalized on when folding the sponge by placing the hydraulic jet side of the fabric to the outside of the sponge.

The continuous length of nonwoven fabric produced in accordance with the present invention and containing the x-ray detectable element is converted into multi-ply surgical sponges using conventional techniques. Typically, a length fabric is cut and folded to provide a 4×4 inch sponge having 3 or more plys. The method of the present invention allows the nonwoven fabric to be produced in wide widths with spaced rows of x-ray detectable elements, and then split into narrower widths as required for the sponge with each such narrower width including one or more x-ray detectable elements. In the manufacturing process, one or more x-ray detectable elements are most conveniently positioned atop fibrous webs linearly in the machine direction and in a spaced relationship. Alternatively, the elements may be laid atop the web in a sinusoidal, circular, or other pattern as desired. In addition, the x-ray detectable element may be discontinuous if desired provided that each finished sponge product contains a sufficient amount of the element to provide adequate detectability in a medical x-ray.

Figure 2:
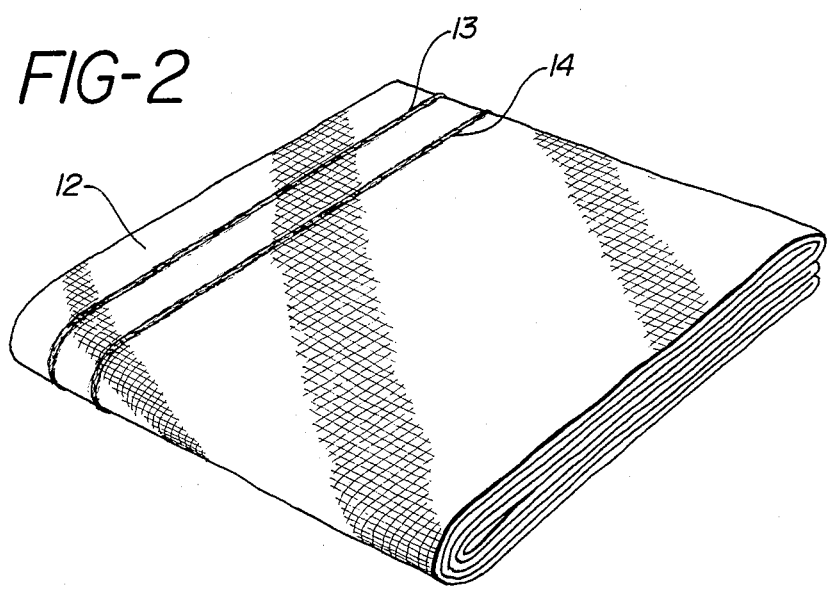
FIG. 2 is a view in perspective of a folded surgical sponge of the present invention.

Referring now to FIG. 2, there is illustrated a surgical sponge according to the present invention comprising a folded, nonwoven fabric 12 which includes integral x-ray detectable elements 13 and 14.

Figure 3:
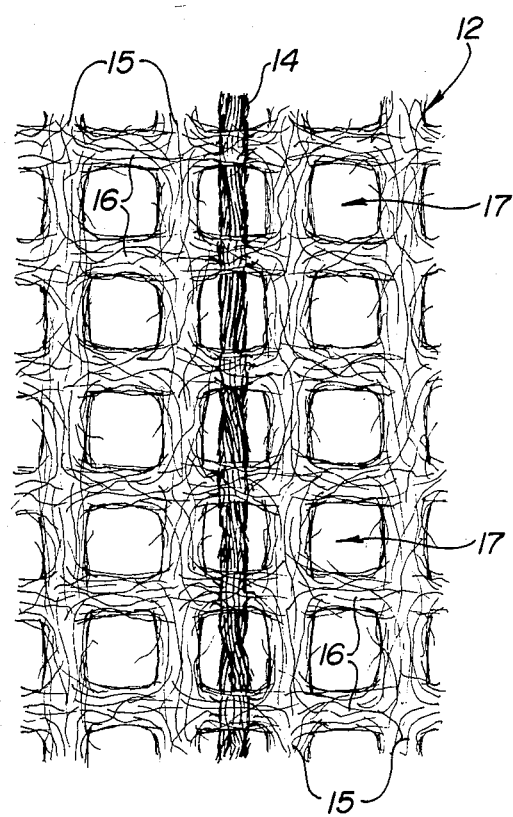
FIG. 3 is an enlarged plan view of a nonwoven fabric comprising the surgical sponge of FIG. 1.

In the entangling process the fibers of the fibrous web are rearranged, crowded, displaced and interspersed by high pressure columnar flow water jets which cause the fiber strands to entangle and interlock to provide significant cohesive strength without the addition of a binder. The nonwoven fabric is formed in a negative image of the supporting belt and depending upon the size and spacing of the apertures in the belt, the appearance of the nonwoven fabric may range from a fine, porous continuous sheet to an open, gauze like material. A representative fabric design illustrated in FIG. 3 is a basic square pattern having equally spaced rows of compacted and entangled fibers 15 and 16 in the machine and cross machine directions respectively. The now entangled radiopaque rovings 13 and 14 are seen to be also entangled with fibers of the fabric, particularly where intersecting with the higher density fibers as in the cross-machine direction. When entangled, the roving itself has greater strength and integrity and substantially no loose fiber ends.

The nonwoven fabrics of the present invention may be constructed of any suitable fibrous material, and in a variety of patterns, all of which is well within the skill of the art. The fibrous material may, for example, be selected from the group consisting of cotton, rayon, cellulosics, acrylics, polyamides, polyesters, polyolefins, and blends thereof. These and other variations in the surgical sponges as described and illustrated herein will be apparent to those skilled in the art and are included within the scope of the present invention.

We claim:

1. A surgical sponge including an integral x-ray detectable element, said sponge comprising a fibrous, nonwoven fabric consisting essentially of entangled fibers arranged in an interconnecting patterned relationship in the plane of the fabric, and at least one x-ray detectable element comprising a roving of radio opaque fibers, said roving being on one surface of said nonwoven fabric and the fibers of said roving being entangled with the fibers of said fabric.

2. A sponge of claim 1 wherein said roving comprises viscose fibers containing from 40 to 65 percent barium sulfate.

3. A sponge of claim 1 wherein said nonwoven fabric comprises at least 2% by weight fusible fibers.

4. A sponge of claim 3 wherein said nonwoven fabric comprises about 90% by weight rayon fibers and 10% by weight polyester staple fibers.

5. A sponge of claim 4 wherein said nonwoven fabric has a weight of from about 30 to 100 g/m$^2$.

6. A sponge of claim 1 wherein the arrangement of said entangled fibers define a substantially rectangular pattern in said nonwoven fabric having from about 8 to 25 openings per inch in both machine and cross-machine directions.

7. Process for making a surgical sponge including an integral x-ray detectable element comprising:

(a) forming a laminate comprising a first "belt side", layer of fibers comprising fusible fibers and other fibers, a second fibrous layer, and an x-ray detectable roving of radiopaque fibers spaced from said first "belt-side" layer;

(b) directing essentially columnar jets of fluid under pressure against said roving and said second layer while supporting said first layer on an apertured belt to intertwine the fibers of the fibrous layers, entangle the fibers of the roving, and intertwine the fibers of the fibrous layers and the fibers of the roving;

(c) applying heat to at least the first layer of said laminate to thermobond the fusible fibers therein.

8. Process for making a surgical sponge including an integral x-ray detectable element comprising:

(a) forming a laminate comprising a first "belt-side", layer of fibers comprising fusible fibers and other fibers, a second fibrous layer, and an x-ray detectable roving of radiopaque fibers spaced from said first "belt-side" layer;

(b) directing essentially columnar jets of fluid under pressure against said roving and said second layer while supporting said first layer on a roll to intertwine the fibers of the fibrous layers, entangle the fibers of the roving, and intertwine the fibers of the fibrous layers and the fibers of the roving;

(c) applying heat to at least the first layer of said laminate to thermobond the fusible fibers therein.

9. The method of claim 7 or 8 wherein said first "belt-side" layer is a carded web of fibers.

10. The process of claim 7 or 8 wherein the fusible fibers in said first layer comprise at least 4% by weight of the first and second fibrous layers.

11. The process of claim 7 or 8 wherein the fusible fibers in said first layer comprise at least 2% by weight of the first and second fibrous layers.

12. The process of claim 7 or 8 wherein said first "belt-side" layer comprises at least about 50% by weight fusible fibers, and comprises about 20% of the combined weight of the first and second fibrous layers.

13. Process for making a surgical sponge including an integral x-ray detectable element comprising:

(a) forming a laminate comprising a web of fibers comprising fusible fibers and other fibers and having a "belt-side" surface and an outside surface, and an x-ray detectable roving of radiopaque fibers overlying said outside surface:

(b) directing essentially columnar jets of fluid under pressure against said roving and said web while supporting the "belt-side" surface of said web on an apertured belt to intertwine the fibers of the web, entangle the fibers of the roving, and intertwine the fibers of the web and the fibers of the roving:

(c) applying heat to at least the "belt-side" surface of said web to thermobond the fusible fibers therein.

14. Process for making a surgical sponge including an integral x-ray detectable element comprising:

(a) forming a laminate comprising a web of fibers comprising fusible fibers and other fibers and having a "belt-side" surface and an outside surface, and an x-ray detectable roving of radiopaque fibers overlying said outside surface:

(b) directing essentially columnar jets of fluid under pressure against said roving and said web while supporting "belt-side" surface of said web on a roll to intertwine the fibers of the web, entangle the fibers of the roving, and intertwine the fibers of the web and the fibers of the roving:

(c) applying heat to at least the "belt-side" surface of said web to thermobond the fusible fibers therein.

15. The method of claim 13 or 14 wherein the fusible fibers are concentrated at the "belt-side" surface of the web.

16. The method of claim 13 or 14 wherein the fusible fibers comprise at least 2% by weight of the fibers of the web.

17. A sponge of claim 3 wherein said fusible fibers are concentrated on the surface of the non-woven fabric opposite the roving of radiopaque fibers.

18. A sponge of claim 3 wherein said fusible fibers are heat fused to form a thermobonded fabric.

* * * * *